United States Patent [19]

Hillman

[11] 4,255,588

[45] Mar. 10, 1981

[54] SYNTHESIS OF CYCLOHEXENE DICARBOXYLIC ACID ESTERS

[75] Inventor: Melville E. D. Hillman, Columbus, Ohio

[73] Assignee: Gulf Oil Corporation, Pittsburgh, Pa.

[21] Appl. No.: 81,500

[22] Filed: Oct. 3, 1979

[51] Int. Cl.$^3$ ............................................ C07C 67/347
[52] U.S. Cl. ..................................................... 560/127
[58] Field of Search ........................................ 560/127

[56] References Cited

PUBLICATIONS

Fiesen et al., Reagents for Organic Synthesis, V. 7, p. 291 (1979).

Primary Examiner—Robert Gerstl
Attorney, Agent, or Firm—Donald R. Cassady

[57] ABSTRACT

A method is provided to manufacture a mixture of 1,4-dicarboalkoxy-1-cyclohexene and 1,3-dicarboalkoxy-1-cyclohexene which can be cyclized and rearranged to isophthalic acid and terephthalic acid.

3 Claims, No Drawings

SYNTHESIS OF CYCLOHEXENE DICARBOXYLIC ACID ESTERS

BACKGROUND OF THE INVENTION

Although the Diels-Alder condensation of dienes with an alkene to form a 6-membered ring compound is well known, and the phosphorous pentoxide dehydration of β-hydroxy alkenes, β-hydroxycarboxylic esters and similar compounds which upon dehydration form conjugated unsaturated systems is equally well known, the concurrent in situ reaction has not been a straight forward reaction. When the starting materials consist of the DABCO catalyzed addition product of acetaldehyde with methyl acrylate and methyl acrylate previous attempts at forming a cyclic diester condensation product have failed. The addition of acetaldehyde to ethyl acrylate in the presence of DABCO, diazabicyclo [2.2.2]-octane, has been shown, U.S. Pat. No. 3,743,669, to yield ethyl α-(1-hydroxyethyl) acrylate. The further reaction of the addition product with a second mole of the acrylate ester to form the 1,5-carboethoxy-1-cyclohexene and 1,4-carboethoxy-1-cyclohexene has not been successful heretofore. The dehydration of lower alkyl α-(1-hydroxyethyl)acrylates by phosphorous pentoxide forms an intractable polymeric product. Attempts to cause a concurrent dehydration-addition by carrying out the dehydration in the presence of a stoichiometric amount of ethyl acrylate were also unsuccessful.

SUMMARY OF THE INVENTION

According to the present invention, a successful method is provided to manufacture a mixture of 1,4-dicarboalkoxy-1-cyclohexene and 1,3-dicarboalkoxy-1-cyclohexene, precursors to the manufacture of terephthalic acid and isophthalic acid. By the method of this invention, a lower-alkyl α-(1-hydroxyethyl) acrylate is dehydrated and reacted with a mole of lower-alkyl acrylate in a Diels-Alder type condensation by adding phosphorous pentoxide dehydrating agent to a mixture of the lower alkyl α-(1-hydroxylower-alkyl)acrylate in at least a 3 mole excess of lower alkyl acrylate as reactant and solvent.

Aromatization and/or rearrangement by methods well known in the art can lead to isophthalic and/or terephthalic acid.

The manufacture of lower alkyl α-(1-hydroxyethyl)acrylates is well known and has been fully disclosed in a patent to Hillman and Baylis, U.S. Pat. No. 3,743,669, issued July 3, 1973. By the method disclosed in the patent, equimolar quantities of the ester and aldehyde are allowed to react in the presence of from 0.1 to about 10% of the catalyst DABCO, diazabicyclo-[2.2.2]-octane, or a simple cyclic tertiary amine having at least one nitrogen atom common to 3 rings, with or without a solvent.

The unsaturated hydroxyester would appear to be easily dehydrated to form the cross conjugated alkylene acrylate ester, which could then undergo the familiar Diels Alder condensation with a second mole of acrylate ester to form a cyclic compound. As indicated hereinabove, all attempts to facilitate this reaction sequence met with failure.

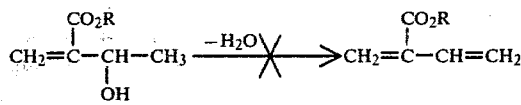

wherein R is lower alkyl By the method of this invention the two steps are carried out as one reaction in high yield by mixing the hydroxy acrylate ester with at least about a 3 mole excess of acrylate and adding to the mixture a sufficient quantity of phosphorous pentoxide to dehydrate the hydroxy ester. The reaction is carried out at from about ambient room temperature to the boiling point of the acrylate ester.

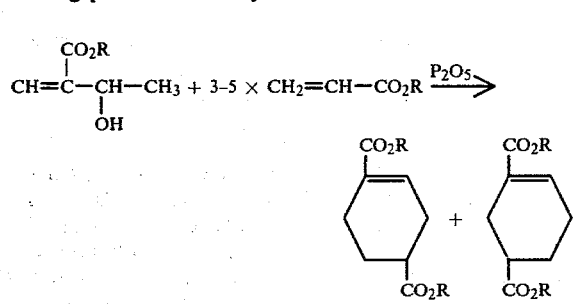

Even higher yields are obtained by carrying out this invention by utilizing a reverse addition of the reactants. Thus, when the hydroxy acrylate ester was added over a period of time (30 minutes to 120 minutes) to a mixture of alkyl acrylate ester and $P_2O_5$ even higher yields were obtained.

The reaction can occur in a solvent as for example dioxane, tetrahydrofuran, acetonitile, methyl ethyl ketone, ethyl acetate, or the like. Preferrably the reaction is carried out without additional solvent.

The reaction is exothermic in nature and is preferrably carried out at room temperature to about 100° C. as for example, the boiling point of ethyl acrylate. It is convenient to control the temperature of the reaction by the slow addition of the phosphorous pentoxide until all has been added. The mixture can then be heated to about 100° C. to complete the reaction.

A catalytic amount, as for example from 0.01 to 0.1 mole percent of hydroquinone can alternatively be added to the reaction solution, but the presence of the catalyst does not substantially alter the reaction or the yield.

Although the examples below are directed to the manufacture of the diethyl 1,5-cyclohex-1-ene dicarboxylate and diethyl 1,4-cyclohex-1-ene dicarboxylate, the method is equally advantageous for any lower alkyl ester. The use of lower alkyl is meant to include methyl, ethyl, n-propyl, and isopropyl esters, or mixed esters.

Thus, the following compound groups can be manufactured by the present process.

dimethyl 1,5-cyclohex-1-ene dicarboxylate and
dimethyl 1,4-cyclohex-1-ene dicarboxylate,
diethyl 1,5-cyclohex-1-ene dicarboxylate and
diethyl 1,4-cyclohex-1-ene dicarboxylate,
di-n-propyl 1,5-cyclohex-1-ene dicarboxylate and
di-n-propyl 1,4-cyclohex-1-ene dicarboxylate,
di-isopropyl 1,5-cyclohex-1-ene dicarboxylate and
di-isopropyl 1,4-cyclohex-1-ene dicarboxylate,
methyl (5-carboethoxy)cyclohex-1-ene carboxylate and
methyl (4-carboethoxy)cyclohex-1-ene carboxylate, ethyl (5-carbomethoxy)cyclohex-1-ene carboxylate and ethyl (4-carbomethoxy)cyclohex-1-ene carboxylate, methyl (5-carbo-isopropoxy)cyclohex-1-ene carboxylate and methyl (3-carbo-isopropoxy)cyclohex-1-ene carboxylate, and the like Isolation of the product is accomplished by extracting the water-soluble byproducts into cold water or a water-ice mixture and drying and distilling the organic phase to recover the excess acrylate ester and the desired cyclohexene dicarboxylate.

DETAILED DESCRIPTION OF THE INVENTION

The present invention will best be understood from the examples which follow which are intended to be illustrative only and not unduly limiting.

EXAMPLE 1

To a mixture of 14.4 g. (0.1 mole) ethyl 2-(1-hydroxyethyl) acrylate and 50 g. (0.5 mole) ethyl acrylate was added 5 g. (0.035 moles) $P_2O_5$. The reaction mixture becomes warm and very viscous. After the addition was complete the reaction mixture was heated to reflux, allowed to reflux for 4 hours, and cooled. After cooling, the reaction mixture was diluted with 250 ml. of diethyl ether, washed twice with saturated aqueous sodium carbonate, dried over anhydrous magnesium sulfate, filtered, evaporated and vacuum distilled.

The fraction boiling at 114°-117° C. at 1 mm.Hg contained the desired product, a mixture of diethyl 1,5-cyclohex-1-ene dicarboxylate and diethyl 1,4-cyclohex-1-ene dicarboxylate. Yield 62 percent.

EXAMPLE 2

To a mixture of 400 g. (4 moles) of ethyl acrylate, 1 g. of hydroquinone, and 115 g. (1 mole) of ethyl α-(1-hydroxyethyl) acrylate was added 40 g. $P_2O_5$ slowly with stirring. The mixture heated and became very viscous (stirrer broke). After addition was complete, heating was commenced and the whole was allowed to reflux for about 4.5 hours. After cooling, 500 ml. of diethyl ether and 100 ml. of water was added. The ether layer was separated and washed twice with portions of 100 ml. of saturated aqueous $Na_2CO_3$ solution, dried and distilled in vaccuo.

Fraction boiling at 125°-132° C. at 3 mm.Hg contained the desired product, a mixture of diethyl 1,5-cyclohex-1-ene dicarboxylate and diethyl 1,4-cyclohex-1-ene carboxylate. Yield 48.8 percent.

EXAMPLE 3

Example 2 was repeated without the addition of hydroquinone. Yield 71.4 percent.

EXAMPLE 4

To a mixture of 125 g. ethyl acrylate and 28.2 g. (0.2 moles) $P_2O_5$, 28.8 g. (0.2 moles) of ethyl 2 (1-hydroxyethyl) acrylate dissolved in 25 ml. ethyl acrylate was added dropwise over a 45-minute period. The reaction mixture became warm and very viscous. After the addition was complete the reaction mixture was allowed to reflux 5 hours and cooled. After cooling, the supernatant solution was decanted and diluted with 300 ml. of diethylether. The ether solution was washed with water, saturated aqueous sodium carbonate, dried over anhydrous magnesium sulfate, the solvents evaporated, and the residue was vacuum distilled.

The fraction boiling at 125°-132° C. at 3 mm.Hg contained the desired product, a mixture of diethyl 1,5-cyclohex-1-ene dicarboxylate and diethyl-1,4-cyclohex-1-ene dicarboxylate. Yield 71.4 percent.

I claim:

1. A method for the manufacture of a mixture consisting of di-lower alkyl 1,5-cyclohex-1-ene dicarboxylate and di-lower alkyl 1,4-cyclohex-1-ene dicarboxylate which comprises reacting lower alkyl 2-(1-hydroxyethyl) acrylate with an excess of lower alkyl acrylate and with phosphorous pentoxide wherein the lower alkyl acrylate acts as a reactant and a solvent for the reaction in the reaction mixture and separating the desired product mixture therefrom.

2. The method of claim 1 wherein the lower alkyl acrylate is present in at least a 3 mol excess.

3. The method of claim 1 wherein at least a catalytic amount of hydroquinone is present in the reaction mixture.

* * * * *